United States Patent [19]

Warren, III et al.

[11] Patent Number: 5,082,780
[45] Date of Patent: Jan. 21, 1992

[54] OLIGONUCLEOTIDE-ENZYME CONJUGATE THAT CAN BE USED AS A PROBE IN HYBRIDIZATION ASSAYS AND POLYMERASE CHAIN REACTION PROCEDURES

[75] Inventors: Harold C. Warren, III, Rush; Fred T. Oakes, Rochester, both of N.Y.

[73] Assignee: Eastman Kodak Company, Rochester, N.Y.

[21] Appl. No.: 406,224

[22] Filed: Sep. 12, 1989

[51] Int. Cl.$^5$ .................. C12N 9/06; C12N 9/04; C07D 207/12; C07D 207/40
[52] U.S. Cl. ................... 435/191; 435/190; 435/192; 548/544; 548/546
[58] Field of Search ............ 435/190, 191, 192; 548/546, 544

[56] References Cited

U.S. PATENT DOCUMENTS

| 4,510,246 | 4/1985 | Wolfe et al. | 435/191 |
|---|---|---|---|
| 4,536,476 | 8/1985 | Wolfe et al. | 435/191 |
| 4,711,964 | 12/1987 | Tan et al. | 548/546 |
| 4,914,210 | 4/1990 | Levenson et al. | 548/413 |
| 4,962,029 | 10/1990 | Levenson et al. | 435/192 |

FOREIGN PATENT DOCUMENTS 89-02932  4/1989  PCT Int'l Appl. .

OTHER PUBLICATIONS

Connolly et al, *Nucl. Acids Res.*, 13(12), pp. 4485–4502 (1985).
Saiki et al, *N. Eng. J. Med.*, 319(9), pp. 537–541 (1988).
Coull et al., *Tetra. Lett.*, 27(34), pp. 3991–3994 (1986).
Jublonski et al, *Nucl. Acids Res.*, 14(15), pp. 6115–6126 (1986).
Connolly, *Nucl. Acids Res.*, 15(7), pp. 3131–3139 (1987).
Sproat et al, *Nucl. Acids Res.*, 15(15), pp. 6181–6196 (1987).
Ruth et al, *Nucleosides and Nucleotides*, 6(1 and 2), pp. 541–542, 1987.

*Primary Examiner*—Douglas W. Robinson
*Assistant Examiner*—Michael Meller
*Attorney, Agent, or Firm*—J. Lanny Tucker

[57] ABSTRACT

A covalent conjugate of an enzyme, such as peroxidase, glucose oxidase, alkaline phosphatase and beta-galactosidase, and an oligonucleotide is herein disclosed. This conjugate can be used as a probe in hybridization assays and in polymerase chain reaction procedures.

4 Claims, No Drawings

OLIGONUCLEOTIDE-ENZYME CONJUGATE THAT CAN BE USED AS A PROBE IN HYBRIDIZATION ASSAYS AND POLYMERASE CHAIN REACTION PROCEDURES

FIELD OF THE INVENTION

This invention relates to a covalent conjugate of an oligonucleotide and an enzyme which is useful in DNA hybridization or polymerase chain reactions. Also provided is a method for preparing this conjugate.

BACKGROUND OF THE INVENTION

The use of single-stranded DNA or RNA probes to test for the presence of particular nucleic acids, and associated organisms and genetic features in biological materials is well known. Among areas in which such probes find usefulness include diagnostic testing of foods, blood and other biological specimens for infectious agents, diagnosis of genetic disorders and the presence of certain diseases such as cancers associated with genetic abnormalities. Non-isotopically labeled synthetic oligonucleotides are widely used in DNA sequencing, DNA hybridization assays, and more recently in amplification procedures, commonly known as polymerase chain reaction procedures described in U.S. Pat. Nos. 4,683,195 (issued July 28, 1987 to Mullis et al) and 4,683,202 (issued July 28, 1987 to Mullis), both incorporated herein by reference.

The principle underlying the use of probes or primers is that under certain conditions, the probe or primer will hybridize by means of hydrogen bonding with a nucleic acid having complementary nucleotides. The hybridized product can then be suitably detected directly or after amplification procedures using appropriate reagents.

Early probes were labeled with radioisotopes such as $^{32}P$-labeled nucleotide triphosphates. However, they are unsuitable for many applications and are generally avoided due to safety and licensing considerations, and because of the natural decay of the label during storage.

Research has been continuing to find suitable labels for probes which do not have such disadvantages, as noted in EP-A-0 278 220 (published Aug. 17, 1988) and U.S. Pat. No. 4,780,405 (issued Oct. 25, 1988 to Kaiser et al). Enzyme labels have become the most generally used labels for labeled oligonucleotides, noted for example in EP-A-0 304 934 (published Mar. 1, 1989).

U.S. Ser. No. 103,978 (filed Oct. 2, 1987 by Levenson et al) and its corresponding WO-A-89/02932 describe the attachment of horseradish peroxidase to an oligonucleotide to form a covalent conjugate. In forming this conjugate, a mercapto-functionalized oligonucleotide is reacted with a maleimide-functionalized horseradish peroxidase. While this procedure represents an advance in the art, further improvements are desired to avoid undesirable side products, such as oxidation products of the mercapto-functionalized oligonucleotide, as well as the expensive and time-consuming preparative steps involved. Moreover, the thiol-functionalized oligonucleotide is unstable and has limited storage life. For maxiumum efficiency, it should be used as soon as it is prepared.

It would be highly advantageous, then, to have a method which would provide an enzyme-labeled oligonucleotide conjugate with improved yields and stability. It would also be desirable to be able to avoid side reactions of the critical oligonucleotide reagent.

SUMMARY OF THE INVENTION

The problems noted above regarding known methods are overcome with a method for preparing a covalent conjugate of an oligonucleotide and an enzyme comprising the steps of:

A. reacting an enzyme which has either a reactive amino group or a group capable of being converted to a reactive amino group, with a blocked mercapto-substituted organic compound which is reactive with the reaction, the organic compound having the structure:

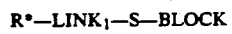

wherein

R* is a group which is capable of reacting with the reactive amino group,

—LINK₁— is a divalent organic moiety, and

—BLOCK is derived from a compound which is capable of reacting with the mercapto group to render the mercapto group non-nucleophilic, which —BLOCK is subsequently removable, to form intermediate A having the structure:

wherein

X—NH— is the enzyme with a hydrogen atom removed from a reactive amino group,

B. removing —BLOCK from intermediate A to form a reagent having the structure:

C. providing an activated oligonucleotide derivative having the structure:

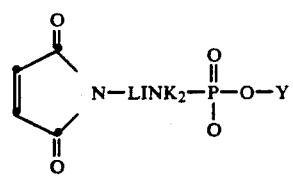

wherein —LINK₂— represents a hydrocarbon chain which may be interrupted or terminated with one or more oxy, thio, imino, carbonylimino, iminocarbonyl, iminocarbonyloxy, phosphate or ureylene groups, and

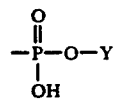

represents an oligonucleotide chain from which a hydroxy group has been removed from the terminal phosphate at the 3' or 5' end thereof, and D. reacting the activated oligonucleotide derivative provided in step C with the reagent formed in step B to form a conjugate having the structure:

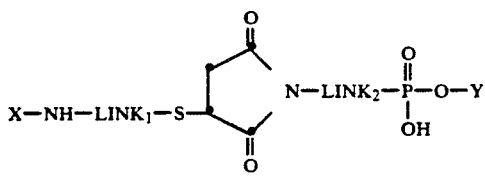

wherein

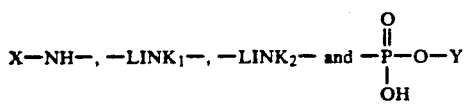

are as defined above.

This invention also provides a covalent conjugate of an enzyme and an oligonucleotide having the structure:

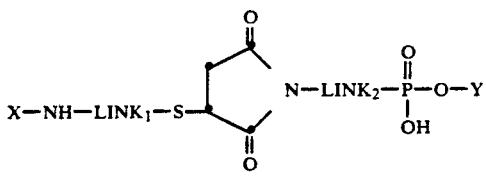

wherein X—NH— represents an enzyme which has either a reactive amino group or a group which is capable of being converted to a reactive amino group, from which a hydrogen atom has been removed from said reactive amino group, —LINK$_1$— represents a divalent organic moiety, —LINK$_2$— represents a divalent hydrocarbon chain which may be interrupted or terminated with one or more oxy, thio, imino, carbonylimino, iminocarbonyl, iminocarbonyloxy, phosphate or ureylene groups, and

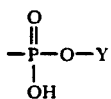

represents an oligonucleotide chain from which a hydroxy group has been removed from the terminal phosphate at the 3' or 5' end thereof.

This invention provides a simplified and rapid means for making an enzyme-labeled oligonucleotide conjugate for use in DNA or RNA assays or amplification procedures. Higher yields of the oligonucleotide-enzyme conjugate are obtained using the procedure of this invention. Also, the activated oligonucleotide derivative, considered the most important reagent in the method, is conserved. This is significant because its preparation is time-consuming and expensive. The production of unwanted side reactions by oxidation is also reduced. The enzyme having a reactive amino group can be converted to a thiol derivative by a simple and inexpensive procedure. This reagent can be used in excess because loss if the reagent by any side reactions is not as critical.

These advantages are achieved by avoiding the use of a thiol-substituted oligonucleotide according to the teaching of WO-A-89/02932. Rather, a reactive thiol group is added to a derivatized enzyme, then reacted with an activated oligonucleotide derivative.

DETAILED DESCRIPTION OF THE INVENTION

As used herein, the term "mercapto-derivatized" refers to a blocked (that is, protected) mercapto group. The mercapto group is spaced apart from the enzyme moiety of the resulting reagent by an organic spacer chain as described herein.

A "blocked" mercapto group refers to one which is protected from chemical reaction while a "blocking" group is present. Such a "blocking" group is subsequently removed or cleaved to allow reaction of the mercapto group.

An oligonucleotide is a single- or double-stranded chain of nucleotides, generally deoxyribonucleotide monomer units. While the reagents and method of the present invention can conceivably be used with a single nucleotide monomer or with a complete DNA molecule, the oligonucleotides used herein are generally single-stranded and have from about 10 to 100 nucleotides. Optimal length of the oligonucleotide will vary depending upon the use of the resulting conjugate.

The covalent conjugate provided by this invention has the general structure:

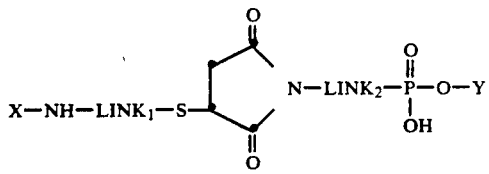

wherein X—NH— represents an enzyme which has either a reactive amino group or a group capable of being converted to a reactive amino group, from which reactive amino group a hydrogen atom has been removed. By "reactive amino group" is meant an amino group which is available and readily reactive with an appropriate reagent (described below).

Enzymes naturally having reactive amino groups can be used in the practice of this invention, and include, but are not limited to, peroxidase, glucose oxidase, alkaline phosphatase, β-galactosidase and urease. The first four enzymes are preferred with peroxidase being most preferred.

Alternatively, the enzyme may be chemically modified in some manner to provide a reactive amino group. This must be done, however, in such a manner as to keep the enzyme moiety reactive with the appropriate substrate so the enzyme will remain suitably detectable and retain its activity.

The enzyme is linked to a maleimide moiety (that is

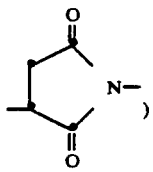

in the conjugate through —LINK$_1$—S— which represents a divalent organic moiety derived from a mercapto-substituted organic compound which is capable of reaction with the reactive amino group of the enzyme. Thus, the mercapto-substituted organic compound has one or more reactive groups such as activated carboxy, anhydride, activated ester or acid halide groups. The —LINK$_1$— moiety can represent any suitable divalent organic moiety having divalent aliphatic (straight chain or saturated carbocyclic), aromatic (such as phenylene) or heterocyclic groups in the chain which can be interrupted with one or more carbonyl, oxy or other non-hydrocarbon moieties as used below to define —LINK$_2$—. Generally, —LINK$_1$— has a molecualr weight in the range of about 28 to about 2000. Preferably, —LINK$_1$— is derived from a mercapto-substituted anhydride, such as S-mercaptosuccinic anhydride.

Also defining the conjugate, —LINK$_2$— represents a divalent hydrocarbon chain which may be interrupted or terminated with one or more oxy, thio, imino, carbonylimino (—CONH—), iminocarbonyl (—NHCO—), iminocarbonyloxy (—NHCOO—), phosphate or ureylene (—NHCONH—) groups. Generally, the hydrocarbon chain has a molecular weight of from about 28 to about 2000 and can be substituted with one or more lower alkyl (1 to 3 carbon atoms, linear or branched) or lower hydroxyalkyl (1 to 3 carbon atoms, linear or branched). Preferably, the hydrocarbon chain is interrupted with at least one oxyethylene group. More preferably, it is terminated with an alkyleneoxy group on the oligonucleotide end, and is terminated on the opposite end with an alkylene group (such as methylene or ethylene).

In the structure of the conjugate above,

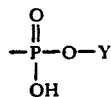

represents an oligonucleotide chain from which a hydroxy group has been removed from the terminal phosphate at the 3' or 5' end thereof. Preferably, the hydroxy group has been removed from the 5' end. Any oligonucleotide can be so attached for use as a probe, primer or other enzyme-labeled molecule for analytical, therapeutic or sequencing purposes.

Preferably, the covalent conjugate of this invention has the structure:

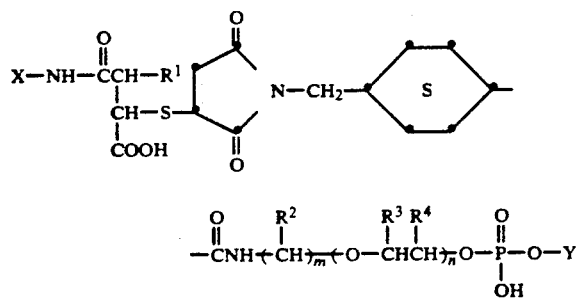

wherein X—NH— represents an enzyme as defined above, R$^1$, R$^2$, R$^3$ and R$^4$ are independently hydrogen, alkyl of 1 to 3 carbon atoms (such as methyl, ethyl, n-propyl or isopropyl) or hydroxyalkyl of 1 to 3 carbon atoms (hydroxymethyl, 2-hydroxyethyl and others apparent to one skilled in the art), m is a positive integer of 2 to 12, n is a positive integer of 1 to 50, and

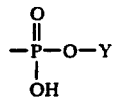

represents an oligonucleotide chain from which a hydroxy group has been removed as defined above.

More preferably, in the foregoing structure, R$^1$, R$^2$, R$^3$ and R$^4$ are independently hydrogen, methyl or hydroxymethyl, m is 2 and n is 1 to 15.

In one preferred conjugate, the enzyme is peroxidase, the oligonucleotide has the sequence:

5'-GAGTGATGAGGAAGAGGAGGGTG-3',

R$^1$, R$^2$, R$^3$ and R$^4$ are each hydrogen, m is 2 and n is 1 to 15. A particularly useful conjugate has the structure:

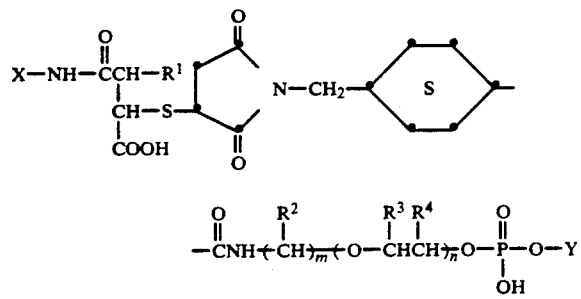

wherein X—NH— is from peroxidase, and R$^1$, R$^2$ R$^3$, R$^4$, m, n and

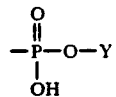

are as defined immediately above.

The conjugate of this invention is prepared using a series of steps which involves reacting derivatized enzymes and oligonucleotides with linking moieties by means of various intermediates which have desired stability, are produced in good yields and do not give unwanted side products.

In the first step of the method of this invention, an enzyme having a reactive amino group (as defined above) is reacted with a blocked (or protected) mercapto-substituted organic compound. Alternatively, if the enzyme does not have the necessary reactive amino group, it can have a group which is capable of being converted to a reactive amino group. The mercapto group is blocked so it will not prematurely react during this step. The organic compound has the structure:

R*—LINK$_1$—S—BLOCK wherein R* is a group which is capable of reacting with the reactive amino group. In some instances, R* leaves the organic compound upon condensation. In other instances, it does not leave the compound, but may be removed from the site which is active in the reaction with the amino group (such as in the case of an anhydride ring opening).

Representative examples of R* include, but are not limited to, halogen (chloro, bromo or iodo), sulfonates (such as p-toluenesulfonate, p-bromobenzenesulfonate, p-nitrobenzenesulfonate, or methanesulfonate), -OCOR [wherein R is an aliphatic (such as methyl, ethyl, isopropyl or pentyl), aromatic (such as phenyl or tolyl) or heterocyclic (such as pyridyl)], carboxylic acid, acyl halide, amide, ester (aliphatic having linear, branched or cyclic groups, or aromatic as defined above), and anhydrides (such as acetic benzoic, succinic and phthalic anhydrides). Preferably, R* is an anhydride, and most preferably, the residue of an aliphatic cyclic anhydride having up to 6 atoms in the ring.

The —LINK₁— group in the organic compound is defined above.

The —BLOCK group is derived from a compound which is capable of reacting with a mercapto group, rendering the mercapto group inactive until —BLOCK has been removed in some manner. Representative —BLOCK moieties include, but are not limited to, —COR' wherein R' represents an aliphatic (linear, branched or cyclic), aromatic or heterocyclic group having a molecular weight of from about 15 to about 200, such as methyl, ethyl, phenyl or pyridyl. Other useful —BLOCK groups are thiopyridyl, 2-carboxy-4-nitrophenylthio, triphenylmethyl or benzoyl. Preferably, —BLOCK is —COR' wherein R' is methyl or phenyl.

Reaction of the organic compound and an enzyme as defined herein is carried out generally under atmospheric pressure at temperatures and for a time sufficient to obtain suitable yield of the resulting intermediate having the structure:

X—NH—LINK₁—S—BLOCK wherein X—NH— is the enzyme with a hydrogen atom removed from a reactive amino group. Generally, the temperature is in the range of from about 0° to about 37° C. and suitable pH conditions are in the range of from about 6 to about 9. These conditions will vary, however, depending upon the enzyme and the organic compound used. For instance, the pH and temperature must be suitable for the enzyme to remain active. The organic compound is at least partially soluble or dispersible in water, or provided in a water-miscible solvent to facilitate dispersion and reaction with the enzyme. Such a solvent must be used in quantities which will not interfere with enzyme reactivity.

The resulting intermediate, however, is not useful as such because of the blocking group attached to the thio group. It is subsequently removed to form a reactive reagent of the structure:

X—NH—LINK₁—SH, wherein X—NH— and —LINK₁— are defined above. Removing the blocking group is generally accomplished by treating the preferred compound with a solution of hydroxylamine and phosphate buffer (pH 7.4) containing ethylenediaminetetraacetic acid. Other conditions for removing a specific blocking group would be readily apparent to one skilled in the art.

An activated oligonucleotide derivative is then provided for reaction. This derivative has the general structure:

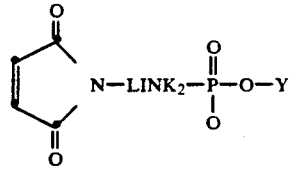

wherein —LINK₂— and

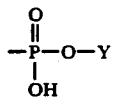

are as defined above.

This activated oligonucleotide derivative can be provided by following the teaching of U.S. Ser. No. 103,978 (noted above), the disclosure of which is incorporated herein by reference. Generally, the conditions of preparing these materials are as follows. An appropriate aminoethylene glycol reagent (with desired chain length) is reacted with phthalic anhydride without solvent at about 200° C. The resulting product is then reacted with a phosphine reagent in methylene chloride at 20°-25° C. This product is then reacted with an appropriate oligonucleotide attached to controlled pore glass using an automated synthesizer (commercially available) and standard procedures to form a derivatized oligonucleotide having a free amino group. The derivatized oligonucleotide is reacted with sulfosuccinimidyl 4-(N-maleimidodomethyl)cyclohexane-1-carboxylate to form the activated oligonucleotide derivative illustrated above.

Lastly, the activated oligonucleotide derivative is reacted with the unblocked enzyme reagent to form the desired conjugate. Reaction conditions for this reaction are generally at about 4° C. in phosphate buffered saline solution (pH 7.4) for about 15 hours although these conditions may be varied for different reagents.

In a preferred embodiment, a method for preparing a covalent conjugate of an oligonucleotide and an enzyme comprises the steps of:

A. reacting an enzyme having a reactive amino group with S-acetylmercaptosuccinic anhydride to form an intermediate having the structure:

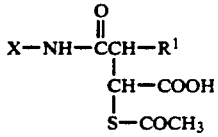

wherein X—NH— represents an enzyme which has a reactive amino group from which a hydrogen atom has been removed, and R¹ is hydrogen, alkyl of 1 to 3 carbon atoms or hydroxyalkyl of 1 to 3 carbon atoms (these groups as defined above), B. reacting the intermediate formed in step A with hydroxylamine to form a reactive mercapto-substituted intermediate having the structure:

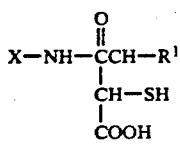

wherein X—NH— and R¹ are as defined above,

C. providing a functionalized oligonucleotide reactant having the structure:

wherein

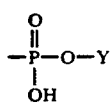

represents an oligonucleotide chain from which a hydroxy group has been removed from the terminal phosphate at the 5' end thereof, $R^2$, $R^3$ and $R^4$ are independently hydrogen, alkyl of 1 to 3 carbon atoms or hydroxyalkyl of 1 to 3 carbon atoms, m is a positive integer of 2 to 12 and n is a positive integer of 1 to 50, D. reacting the reactant provided in step C with sulfosuccinimidyl 4-(N-maleimidomethyl)cyclohexane-1-carboxylate to form an activated oligonucleotide derivative, and E. reacting the activated oligonucleotide derivative formed in step D with the intermediate formed in step B to form a conjugate having the structure:

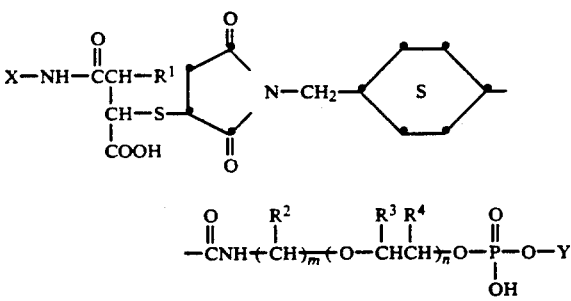

wherein X—NH—, $R^1$, $R^2$, $R^3$, $R^4$, m, n and

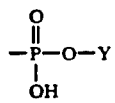

are as defined above.

In this embodiment, most preferably, each of $R^1$, $R^2$, $R^3$ and $R^4$ is hydrogen, m is 2, n is 1 to 15, X—NH— is derived from peroxidase.

The specific conditions for carrying out this preferred embodiment are described in detail in the illustrative Examples below. However, it should be understood that other embodiments using other reagents would similarly be possible using the general conditions described above. Thus, the examples are not to be considered limiting.

EXAMPLE 1

Preparation of Peroxidase Oligonucleotide Conjugate

A conjugate having horseradish peroxidase covalently attached to a single-stranded oligonucleotide was prepared in this example.

Materials

Various reagents were obtained commercially as follows: horseradish peroxidase from Sigma Chemical Co., S-acetylmercaptosuccinic anhydride from Aldrich Chemical Co, sulfosuccinimidyl 4-(N-maleimidomethyl)cyclohexane-1-carboxylate from Pierce Chemical Co., aminotriethyleneglycol from Texaco, chloro-2-cyanoethoxy-N,N-diisopropylaminophosphine from American Bionetics (Hayward, Calif.), and all other reagents from Eastman Kodak or Aldrich Chemical.

The oligonucleotide used in this example had the sequence shown below where A, T, G and C represent the four standard deoxyribonucleoside triphosphate components:

5'-GAGTGATGAGGAAGAGGAGGGTG-3' and was attached to —LINK₂— through its 5' hydroxyl group.

Various materials and equipment were obtained as follows: Biosearch 8700 DNA Synthesizer from Milligen/Biosearch, controlled pore glass support from Biosearch, SpectroPor ™ 2 dialysis bag from Spectrum Medical Ind. (Los Angeles, Calif.), stirred cell concentrator from Amicon (Danvers, Mass.), PD-10 and NAP-10 columns from Pharmacia (Uppsala, Sweden), and a DEAE-agarose column from Waters.

Preparation

Step 1

Preparation of Mercapto-Substituted Enzyme Reagent

Horseradish peroxidase (100 mg dry weight) was dissolved in sodium carbonate (13.4 ml, 0.1 molar, pH 9.5) at 4° C. and reacted with a solution of S-acetylmercaptosuccinic anhydride in dry N,N-dimethylformamide (300 μl at 17.4 mg/ml) for one hour at 4° C. or lower. This mixture was transferred by pipette into a SpectorPor ™ 2 dialysis bag that had been prewet with deionized distilled water for 10 minutes. The bag was then placed into phosphate buffered saline solution (pH 7.4) using 50 times the volume of the reaction mixture, and slowly stirred at 4° C. for about four hours. The solution volume was concentrated using an Amicon concentrator to give 20–30 mg/ml of the desired intermediate.

This intermediate (1.34 ml of solution containing 41.85 mg/ml of phosphate buffered saline solution, pH 7.4) was unblocked by reaction with a solution containing hydroxylamine (1.2 ml, 0.25 molar) in phosphate buffer (0.1 molar, pH 7.4), and ethylenediaminetetraacetic acid (0.001 molar) for two hours at 20°–25° C. The resulting product was purified by chromatography using a PD-10 column and phosphate buffered saline solution (pH 7.4) as the eluent. The product (about 54 mg) was then used immediately in Part 3 below.

Part 2

Preparation of Activated Oligonucleotide Derivative

Aminotriethylene glycol (100 g) and phthalic anhydride (100 g) were mixed together and heated neat with stirring under nitrogen to 205° C., then cooled to room temperature. The resulting product was obtained as an oil which slowly solidified. The material was recrystalized from ethyl acetate (250 ml) to give 118 g of white crystalline product. The structure was confirmed by nuclear magnetic resonance spectroscopy.

This product (5 g) was dissolved in methylene chloride (50 ml), N,N-diisopropylethylamine (3 equivalents, 9.3 ml) was added, followed by chloro-2-cyanoethoxy-N,N-diisopropylaminophosphine (1.1 equivalents, 4.65 g) and the mixture was stirred at 20°-25° C. for 30 minutes. The reaction mixture was extracted with ethyl acetate (twice with 50 ml) and washed twice with water (50 ml), and concentrated using a rotary evaporator to give an oil (8.1 g). The material was 95% pure by nuclear magnetic resonance and mass spectral analysis. It was used as is in the next step. This product (500 μl of a solution of 4 g/70 ml of acetonitrile) was reacted with an oligonucleotide identified above (1 μmolar) in acetonitrile using the automated synthesizer, controlled pore glass and the procedures identified above. The last step consisted of hydrolysis with ammonium hydroxide to remove the oligonucleotide from the controlled pore glass and to unblock the amine to form an amino-derivatized, oligonucleotide reagent.

This reagent (OD 55 at 260 nm) was dissolved in deionized distilled water (500 μl) and cooled to 4° C. Sodium carbonate (50 μl of 1 molar solution, pH 8) was added to buffer the reaction. Sulfosuccinimidyl 4-(N-maleimidomethyl)cyclohexane-1-carboxylate (11.25 mg in 100 μl N,N-dimethylformamide) and water (100 μl) were added and the reaction mixture was rotated end-over-end at 4° C. for one hour. The resulting product was purified by chromatography using a NAP-10 column and phosphate buffered saline solution (pH 7.4) as the eluent. About 50 OD of product was obtained.

Part 3

Reaction of Derivatized Oligonucleotide with Enzyme Reagent

The activated oligonucleotide derivative described above (about 50 OD in 1.5 ml of phosphate buffered saline solution, pH 7.4) was added to the mercapto-substituted enzyme reagent prepared as described above (about 54 mg in 3.5 ml of buffered solution). The total volume was reduced to about 0.5 ml using an Amicon concentrator. The reaction mixture was then rotated end-over-end at 4° C. for 15 hours, followed by dilution to 5 ml with tris(hydroxymethyl)aminomethane buffer (0.02 molar, pH 8), and chromatographed on a DEAE-agarose column using as eluents: first with tris(hydroxymethyl)aminomethane buffer (pH 8), then with the buffer (0.02 molar) containing sodium chloride (1 molar). The fractions having an absorption ratio ($A_{260}/A_{403}$) of about 3.2 were combined and stored in phosphate buffered saline solution (pH 7.5) at a concentration of 1.5 OD/ml as the desired peroxidase-oligonucleotide covalent conjugate of this invention.

EXAMPLES 2-6

Preparation of Various Conjugates

These examples were carried out like Example 1 to prepare various conjugates having different oligonucleotides. These oligonucleotides are listed as follows by their sequences:

Example 2

5'-UTTTGGTCCTTGTCTTATGTCCAGAATGC-3'

Example 3

5'-TAGTAGCCAGCTGTGATAAATGTCAGC-TAAAAGGAGAAGCC-3'

Example 4

5'-ACGGTACAGGCCAGACAATTATTGTCTG-GTATAGT-3'

Example 5

5'-GAGACCATCAATGAGGAAGCT-GCAGAATGGGAT-3'

Example 6

5'-ATCCTGGGATTAAATAAAATAG-TAAGAATGT-3'

The invention has been described in detail with particular reference to preferred embodiments thereof, but it will be understood that variations and modifications can be effected within the spirit and scope of the invention.

We claim:

1. A covalent conjugate of an enzyme and an oligonucleotide having the structure:

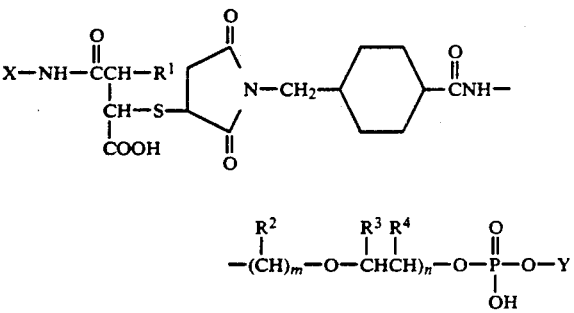

wherein X—NH— represents an enzyme having a reactive amino group from which a hydrogen atom has been removed, $R^1$, $R^2$, $R^3$ and $R^4$ are independently hydrogen, alkyl of 1 to 3 carbon atoms or hydroxyalkyl of 1 to 3 carbon atoms, m is a positive integer of 2 to 12, n is a positive integer of 1 to 50, and

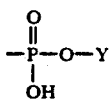

represents an oligonucleotide chain from which a hydroxy group has been removed from the terminal phosphate at the 3' or 5' end thereof.

2. The conjugate of claim 1 wherein said enzyme is peroxidase, and said oligonucleotide is attached to said conjugate at the 5' end.

3. The conjugate of claim 1 wherein $R^1$, $R^2$, $R^3$ and $R^4$ are independently hydrogen, methyl or hydroxymethyl, m is 2 and n is 1 to 15.

4. The conjugate of claim 1 wherein said enzyme is selected from the group consisting of peroxidase, glucose oxidase, alkaline phosphatase and β-galactosidase.